United States Patent
Hanlon et al.

(10) Patent No.: US 7,727,750 B2
(45) Date of Patent: Jun. 1, 2010

(54) BIOCATALYTIC ASYMMETRIC REDUCTION IN PREPARATION OF (S)-N-[5-(1,2-DIHYDROXY-ETHYL)-PYRAZINYL]-2,2-DIMETHYL-PROPIONAMIDE

(75) Inventors: Steven Paul Hanlon, Bottmingen (CH); Hans Iding, Rheinfelden (DE); Ernst Kupfer, Zurich (CH); Roumen Nikolaev Radinov, West Caldwell, NJ (US); Lianhe Shu, Livingston, NJ (US); Ping Wang, Nutley, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 92 days.

(21) Appl. No.: 12/061,925

(22) Filed: Apr. 3, 2008

(65) Prior Publication Data
US 2008/0248537 A1 Oct. 9, 2008

(30) Foreign Application Priority Data
Apr. 4, 2007 (EP) .................................. 07105615

(51) Int. Cl.
*C12P 17/12* (2006.01)
*C12P 1/04* (2006.01)
*C07D 241/00* (2006.01)
(52) U.S. Cl. ..................... 435/122; 435/170; 435/189; 435/195; 435/219; 435/196; 435/255.1
(58) Field of Classification Search ................. 435/122, 435/189, 195, 219, 196, 255.1; 544/336, 544/335

See application file for complete search history.

(56) References Cited

FOREIGN PATENT DOCUMENTS
WO WO 2004/052869 A1 6/2004

OTHER PUBLICATIONS

G. Egri et al., *Tetrahedron Asymmetry* 1998, 9, 271-283.
Kometani et al, *J. Bioscience. Bioeng.* 2001, 91, 525-527.
Z-L Wei et al, *Bioorganic and Medicinal Chemistry* 2000, 8, 1129-1137.
V. Kren et al., *Angew. Chem. Int. Ed. Engl.* 1995, 34 (8), 893.
*Tetrahedron Asymmetry* 2006, 17, 47-52, Z. Liu et al.
Kaluzna, I.A. et al, *Tetrahedron:Asymmetry*, (2005) 16: 3682-3689.
Zhu, D. et al, *Tetrahedron: Asymmetry*, (2005) 16: 3275-3278.

*Primary Examiner*—Sandra Saucier
*Assistant Examiner*—Susan Hanley
(74) *Attorney, Agent, or Firm*—George W. Johnston; Dennis P. Tramaloni; Samuel H. Megerditchian

(57) ABSTRACT

The present invention relates to biocatalytic asymmetric reduction for the preparation of 2-amino-[5-(1-hydroxy-2-hydroxy or halogen-ethyl)]-pyrazine derivatives of the formula

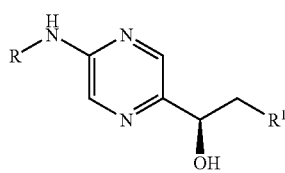

wherein R is lower alkylcarbonyl or an amino protecting group and $R^1$ is hydroxy or halogen. The compounds are key intermediates in the manufacture of a glucokinase activator.

13 Claims, No Drawings

US 7,727,750 B2

BIOCATALYTIC ASYMMETRIC REDUCTION IN PREPARATION OF (S)-N-[5-(1,2-DIHYDROXY-ETHYL)-PYRAZINYL]-2,2-DIMETHYL-PROPIONAMIDE

PRIORITY TO RELATED APPLICATION(S)

This application claims the benefit of European Patent Application No. 07105615.4, filed Apr. 4, 2007, which is hereby incorporated by reference in its entirety.

FIELD OF THE INVENTION

The present invention relates to a process for the preparation of 2-amino-[5-(1-hydroxy-2-hydroxy or halogen-ethyl)]-pyrazine derivatives of the formula

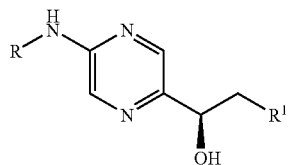

All documents cited to or relied upon below are expressly incorporated herein by reference.

BACKGROUND

One of the key building blocks used in the synthesis of the compound of formula III are enantiomerically pure 2-amino-[5-(1,2-dihydroxy-ethyl)]-pyrazine derivatives of the formula

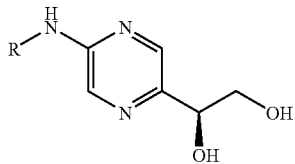

wherein R is lower alkylcarbonyl or an amino protecting group. For the preparation of active pharmaceutical ingredients (APIs) it is absolutely necessary to use isomerically pure building blocks and/or highly stereoselective procedures, because side components in APIs may have adverse effects in the treatment of illnesses. Therefore, a high purity is requested for all APIs.

SUMMARY OF THE INVENTION

In an embodiment of the present invention, provided is a process for the preparation of compounds of formula I:

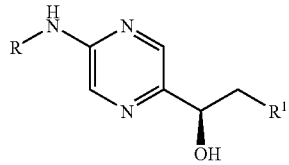

wherein R is lower alkylcarbonyl or an amino protecting group and $R^1$ is hydroxy or halogen, by enzymatic hydrolysis and/or enzymatic asymmetric reduction of a ketone of the formula

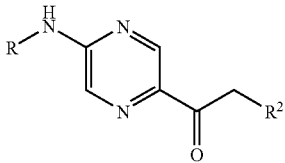

wherein $R^2$ is lower alkylcarbonyloxy or halogen.

In another embodiment of the present invention, provided is a compound of formula:

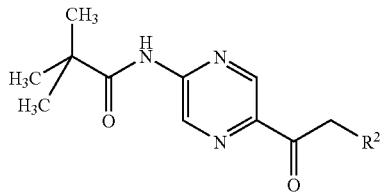

wherein $R^2$ is lower alkylcarbonyloxy or halogen,

In a further embodiment of the present invention, provided is a compound of formula:

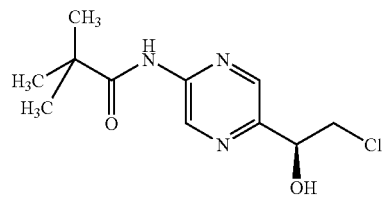

In an another embodiment of the present invention, provided is a process for the preparation of a compound of the formula:

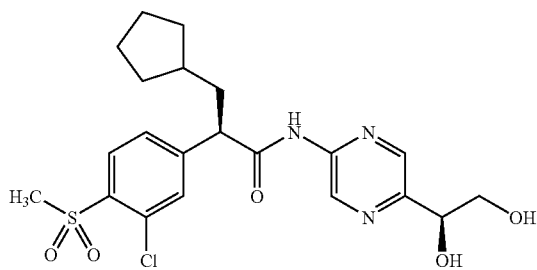

comprising the process according to the steps above, followed by
a) reaction of the diol of formula Ia

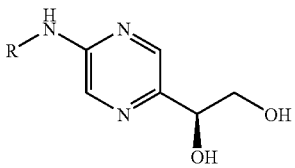

wherein R is lower alkylcarbonyl or an amino protecting group, with 2,2-dimethoxypropane to form an acetal and deprotection of the amine under basic conditions to obtain a compound of formula

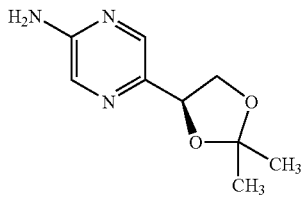

IV b) condensation of the amine of formula IV with the carboxylic acid of formula

V

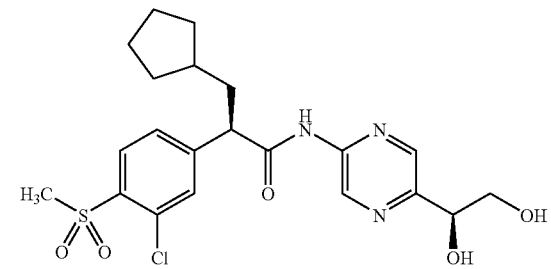

or an activated derivative thereof to obtain the amide; and
c) hydrolysis of the acetal under acidic conditions.

DETAILED DESCRIPTION

The present invention is useful in the preparation of enantiomerically pure (S)—N-[5-(1,2-dihydroxy-ethyl)-pyrazinyl]-2,2-dimethyl-propionamide. This compound is an intermediate for a glucokinase activator, 2-(3-chloro-4-methanesulfonyl-phenyl)-3-cyclopentyl-N-[5-(1,2-dihydroxy-ethyl)-pyrazin-2-yl]-propionamide, of the formula III which is useful for the treatment and/or prophylaxis of type II diabetes:

III

The compound of formula III is disclosed in PCT International Patent Application No. WO 2004/052869 A1, Optically active 1,2-diols are versatile synthetic intermediates and difficult to obtain in enantiomerically pure form. The method described in WO 2004/052869 A1 for preparing (S)—N-[5-(1,2-dihydroxy-ethyl)-pyrazinyl]-2,2-dimethyl-propionamide involved Sharpless oxidation of the corresponding vinyl pyrazine precursor in a reaction comprising osmium tetroxide (see scheme 1). This reaction is not possible on multi-kg scale due to the toxicity of the osmium tetroxide catalyst. Thus, the problem to be solved was to find a suitable process alternative which is free of toxic reagents and can be carried out on large technical scale.

Scheme 1

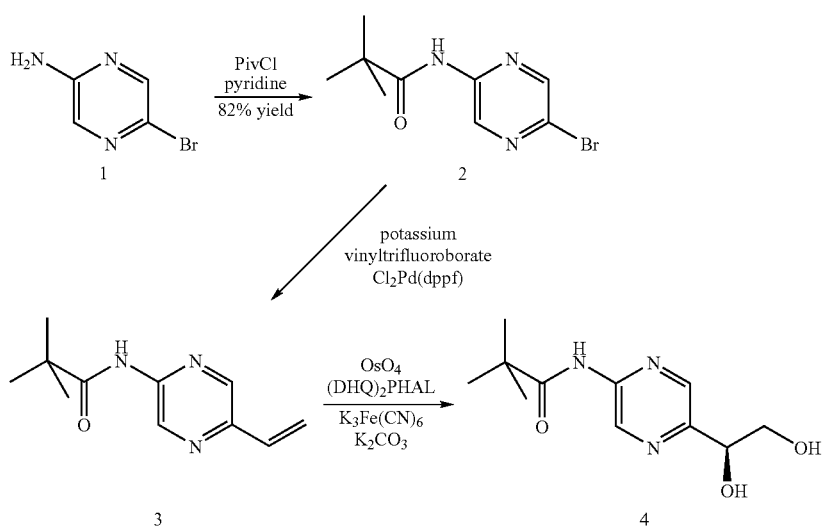

There are few literature examples reporting microbial hydrolysis/reduction of alkoxy ketones to the corresponding diols in a single step. G. Egri et al., *Tetrahedron Asymmetry* 1998, 9, 271-283, describe the biotransformation of a series of 1-acetoxy-3-aryloxypropan-2-ones by bakers yeast. Out of 13 ketones tested only two were transformed directly to the diol with no formation of the intermediate monoacetate. In most cases a mixture of monoacetate and diol was seen which is undesirable for the process for the preparation of compounds of formula I. In addition these reactions were only carried out on the 0.5 g scale at a substrate concentration of 0.25% w/w; far below that to be used for the manufacture of compounds of formula I.

T. Kometani et al, *J. Bioscience. Bioeng.* 2001, 91, 525-527, describe the preparation of (S)-1,2-propanediol by reduction of 1-acetoxy-2-propanone using bakers yeast. Although conversion to the diol was complete at 1% w/v substrate concentration the ee was 88%. This value could only be improved by suppressing the hydrolysis of the acetoxy ketone.

Z-L Wei et al, *Bioorganic and Medicinal Chemistry* 2000, 8, 1129-1137, describe the preparation of S-diols from the corresponding 2-acetoxy-1-arylethanones but again the selectivities were relatively low and the monoacetates were in most cases present.

The ee of the (S)-diol formed by the microbial reduction/hydrolysis reaction is a crucial value as it influences the final yield of API. In case of the API as prepared according to the present invention the subsequent ketalization and crystallization steps led to an increase of the enantiomeric excess to >99%.

Beside the described microbial biotransformation for the hydrolysis/reduction of an alkoxy ketone one might apply only the necessary isolated biocatalyst—enzymes (e.g. a hydrolase, a ketoreductase, a glucose dehydrogenase)—in a one pot approach. The asymmetric reduction by isolated ketoreductases in combination with the enzymatic cofactor recycling using glucose dehydrogenase and enzymatic hydrolysis of ester moieties are state of the art. S. Kambourakis et al., *Tetrahedron Asymmetry* 2005, 16, 3682-3689, describe the reduction of 2-hydroxy-1-phenyl-ethanone using different ketoreductases. Enzymatic transformations employing two or more enzyme types are frequently successful as described in V. Kren et al., *Angew. Chem. Int. Ed. Engl.* 1995, 34 (8), 893. Therefore, an upstream enzymatic hydrolysis of an acetoxy ketone into a hydroxyl ketone and a downstream reduction of this in situ generated hydroxyl ketone mimics the potential microbial—hydrolysis/reduction—biotransformation. The multi enzymatic reaction using isolated enzymes display some advantages such as i) standard equipment might be used; ii) high reaction rates, iii) no side activities in comparison with whole cell systems, iv) simple reaction control, and v) higher yield in the subsequent ketalization reaction due to the higher ee of the (S)-diol produced.

The terminal position of 2-amino-[5-(acetyl)]-pyrazine derivatives might have different substituents, which are convertible into a hydroxyl function after the asymmetric reduction of the ketone moiety. For a halogen substituents, or more specifically, the chloro substituent, one potential candidate, several biocatalytic asymmetric reductions of different aryl ketones are described in literature, L. Hua et al., *Organic & Biomolecular Chemistry* 2006, 4, 2690-2695 and L. Hua et al. *Tetrahedron Asymmetry* 2005, 16, 3275-3278. The synthesis of enantiomerically pure 1,2-diols starting from aromatic chlorinated alcohols is described via corresponding enantiomerically pure epoxide in T. Ikaraiya et al., *Tetrahedron* 2004, 60, 7411-7417 and subsequent epoxide hydrolysis either via biocatalytic hydrolysis as described in Z. Li et al., *Tetrahedron Asymmetry* 2006, 17, 47-52 or via hydrolysis using metal catalysis as described in G-J. Kim et al., *Tetrahedron Letters* 2005, 46, 2263-2266.

With the biotransformation processes according to the present invention an efficient procedure for the preparation of enantiomerically pure 2-amino-[5-(1,2-dihydroxy-ethyl)]-pyrazine derivatives has been found.

Unless otherwise indicated, the following definitions are set forth to illustrate and define the meaning and scope of various terms used to describe the invention herein.

In this specification the term "lower" is used to mean a group consisting of one to six, preferably of one to four carbon atom(s).

The term "halogen" refers to fluoro and chloro, with chloro being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_6$-alkyl", atone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, tert-butyl, n-pentyl, 3-methylbutyl, n-hexyl, 2-ethylbutyl and the like. Preferable lower alkyl residues are methyl, ethyl and tert-butyl, with tert-butyl being especially preferred.

The term "lower alkylcarbonyl" refers to the group —C(O)—R', wherein R' is a branched or straight-chain monovalent alkyl radical of one to six carbon atoms, preferably one to four carbon atoms. Preferred "lower alkylcarbonyl" or "$C_1$-$C_6$-alkylcarbonyl" groups are acetyl, propionyl, butyryl, pivaloyl, pentanoyl and hexanoyl.

More preferred are acetyl and pivaloyl (tert-butylcarbonyl), with tert-butylcarbonyl being most preferred.

The term "amino protecting group" as used herein refers to a substituent commonly employed to block or protect the amino functionality while reacting other functional groups on the compound. Suitable amino protecting groups are selected from the group consisting of the formyl group, the benzyl group, ester groups such as benzyloxycarbonyl ("Cbz"), 9-fluorenylmethoxycarbonyl ("FMOC"), tert-butoxycarbonyl ("BOC") and allyloxycarbonyl, and arylsulfonyl derivatives such as para-toluenesulfonyl, benzylsulfonyl and phenylsulfonyl. The selection and use (addition and subsequent removal) of amino protecting groups is well known to the skilled in the art. Further examples of groups referred to by the above terms are described by T. W. Greene and P. G. M. Wuts, Protective Groups in Organic Synthesis, 3$^{rd}$ edition, John Wiley and Sons, New York, N.Y., 1999. A preferred amino protecting group is BOC.

The term "lower alkylcarbonyloxy" refers to the group —O—C(O)—R", wherein R" is a straight-chain monovalent alkyl radical of one to six carbon atoms, preferably one to four carbon atoms.

Preferred "lower alkylcarbonyloxy" or "$C_1$-$C_6$-alkylcarbonyloxy" groups are acetyloxy, propionyloxy, butyryloxy, pentanoyloxy and hexanoyloxy. Especially preferred "lower alkylcarbonyloxy" is acetyloxy.

The term "enantiomerically pure" refers to a composition that comprises at least 90%, preferably about 95% to 100%, more preferably 98% to 100%, and most preferably 99% to 100% of a single enantiomer of that composition.

The term "enantiomeric excess" (abbreviated "ee"), as used herein is defined as [F(+)−F(−)], wherein F(+) refers to the mole or weight fraction of the (+)-enantiomer and F(−) refers to the mole or weight fraction of the (−)-enantiomer. Correspondingly, the term "percent enantiomeric excess" or "% ee" is defined as 100×[F (+)−F (−)]. Alternatively, the percent enantiomeric excess can be calculated as 100×([R]−[S]/[R]+[S]).

The present invention refers to a process for the preparation of compounds of the formula

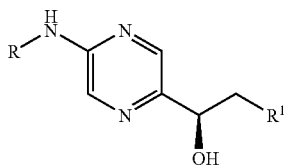

I wherein R is lower alkylcarbonyl or an amino protecting group and $R^1$ is hydroxy or halogen, by enzymatic hydrolysis and/or enzymatic asymmetric reduction of a ketone of the formula

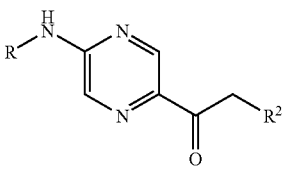

II wherein $R^2$ is lower alkylcarbonyloxy or halogen.

In a preferred embodiment of the invention, the process is characterized in that $R^1$ is hydroxy and $R^2$ is acetyloxy, meaning a compound of formula

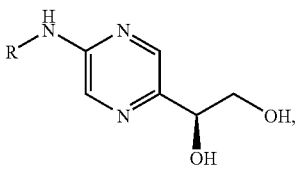

Ia wherein R is lower alkylcarbonyl or an amino protecting group, is obtained.

In one embodiment of the invention, the process is characterized in that the enzymatic hydrolysis and the enzymatic asymmetric reduction is performed together with a yeast of the species Candida parapsilosis, Thus, the invention refers to a process for the preparation of 2-amino-[5-(1,2-dihydroxy-ethyl)]-pyrazines of the formula

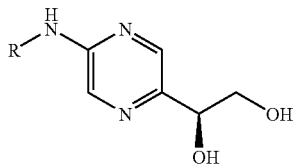

Ia wherein R is lower alkylcarbonyl or an amino protecting group, by enzymatic hydrolysis and enzymatic asymmetric reduction with a yeast of the species Candida parapsilosis of a keto compound of the formula

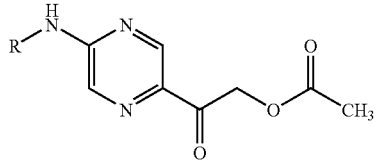

IIa

By using a strain of the yeast Candida parapsilosis the desired product Ia is produced by hydrolysis and asymmetric reduction of the corresponding acetoxy ketone IIa at a technically relevant substrate concentration. The process can be carried out without addition of a hydrolyzing enzyme such as a lipase because the strain can catalyze both hydrolysis and asymmetric reduction.

In detail, the invention relates to a scalable biocatalytic process comprising hydrolysis and asymmetric microbial reduction of the compound of formula IIa using the yeast Candida parapsilosis to obtain an enantiomerically pure (S)-diol of the formula Ia, comprising the steps a) Growing a culture of Candida parapsilosis at 27 to 30° C. for 1 to 2 days in flasks or fermenters containing a rich media comprising; yeast extract (1% w/v), soytone (1% w/v), yeast nitrogen base (0.67% w/v) and glucose (2% w/v);

b) Adding of $NH_4OH$ 16 to 20 h after inoculation in order that the pH is maintained in the range of 6.5 to 7.0 and feeding of ethanol equivalent to 3 to 5% (v/v) per 24h in order to provide reducing equivalents for growth and for the asymmetric reduction;

c) After a further 2 to 4 hours adding of 175 g of the acetoxy ketone substrate of formula IIa to the fermentation broth as a suspension in 875 ml water to give a final concentration of 1 to 5% (w/v);

d) Hydrolysis and reduction of the acetoxy ketone of formula IIa to the corresponding (S)-diol within 2 to 5 days;

e) Isolation of the (S)-diol by separation of the biomass (centrifugation) followed by extraction of the (S)-diol with ethyl acetate (3 times with 2 volume equivalents) and concentration.

The reaction must also proceed to completion, i.e. all the substrate must be converted, at a substrate concentration of 5% (w/v), which is considerably higher than the concentration quoted in the literature examples.

By biotransformation of the acetoxy ketone of formula IIa with C. parapsilosis enantiomeric pure (S)-diol with an ee in the range of 91.4% to 95.6% is obtained.

As used herein, Candida parapsilosis is a strain isolated at Roche and deposited under the Budapest treaty on Mar. 9, 2007, at DSMZ (Deutsche Sammlung von Mikroorganismen und Zellkulturen GmbH, Inhoffenstrasse 7B, 38124 Braunschweig, Germany) under accession number DSM 19155. Several other strains of C. parapsilosis also catalyzed the described biotransformation resulting in (S)-diol with ee of 92 to 95% indicating that any C. parapsilosis strain can potentially be used. In addition, strains of the yeasts Candida kefyr, Kluyveromyces marxianus and the fungus Calonectria rigidiuscula can be used.

In a preferred embodiment, the invention relates to a scalable biocatalytic process comprising asymmetric microbial reduction of acetic acid 2-[5-(2,2-dimethyl-propioylamino)-pyrazin-2-yl]-2-oxo-ethyl ester (the compound of formula IIa, wherein R is tert-butylcarbonyl) and hydrolysis using the yeast *Candida parapsilosis* to obtain enantiomerically pure (S)—N-[5-(1,2-dihydroxy-ethyl)-pyrazinyl]-2,2-dimethyl-propionamide.

In a further embodiment of the invention, the process is characterized in that the enzymatic hydrolysis is performed by means of a hydrolase (EC 3.1.1) selected from the group consisting of an esterase, a protease or a lipase and that the subsequent enzymatic asymmetric reduction is performed by means of one or more oxidoreductases (EC 1.1.1). Thus, the invention also refers to a process for the preparation of 2-amino-[5-(1,2-dihydroxy-ethyl)]-pyrazines of the formula

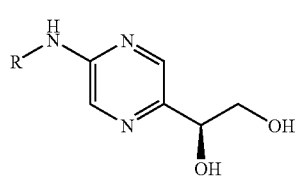

Ia wherein R is lower alkylcarbonyl or an amino protecting group, by enzymatic hydrolysis by means of an enzyme selected from the group consisting of a hydrolase, an esterase, a protease or a lipase and enzymatic asymmetric reduction by means of one or more oxidoreductases of a keto compound of the formula

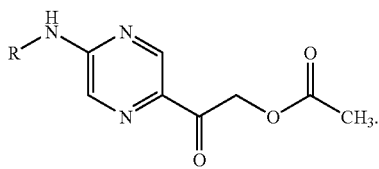

IIa

Preferably, the enzymatic hydrolysis is performed by means of a lipase. More preferably, the lipase is obtained from *Candida Antarctica, Alcaligenes* sp, or *Burkholderia cepacia*.

In a preferred embodiment, a ketoreductase or an alcohol dehydrogenase is used as oxidoreductase in the enzymatic asymmetric reduction.

The multi enzymatic biotransformation is transformed as one pot reaction. The hydrolysis—deacetylation—is carried out by contacting a hydrolase with the acetoxy ketone of formula IIa suspended in a biphasic reaction media. The reduction is carried out by contacting an oxidoreductase with the in situ formed α-hydroxy ketone. Due to the low stability of the in situ formed α-hydroxy ketone the applied reactivity of the reductases has to be in excess of the applied reactivity of the hydrolase. The required reducing equivalents are applied in catalytic amounts and are recycled in situ. The desired product of formula Ia is produced at technical reaction conditions.

In a preferred embodiment, the invention relates to a scalable biocatalytic process comprising hydrolysis of acetic acid 2-[5-(2,2-dimethyl-propioylamino)-pyrazin-2-yl]-2-oxo-ethyl ester (the compound of formula IIa, wherein R is tert-butylcarbonyl) by means of an enzyme selected from the group consisting of a hydrolase, an esterase, a protease or a lipase and enzymatic asymmetric reduction by means of one or more oxidoreductases to obtain enantiomerically pure (S)—N-[5-(1,2-dihydroxy-ethyl)-pyrazinyl]2,2-dimethyl-propionamide.

Scheme 2

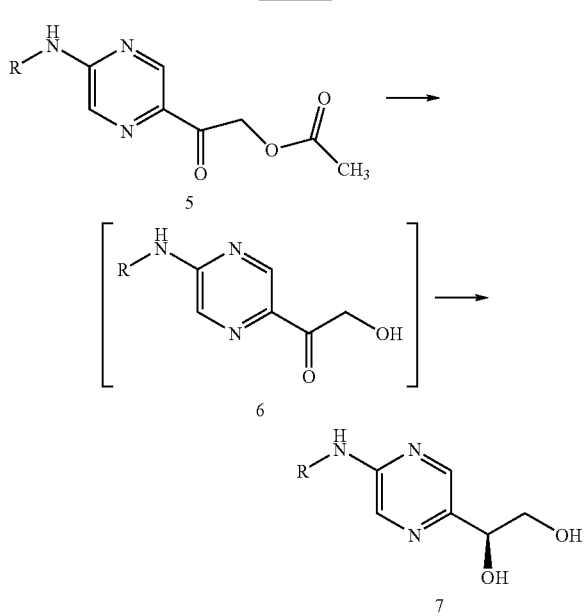

The first step, the in situ generation of the hydroxyl ketone (6) by deacetylation of the acetoxy ketone (5) is carried out by hydrolases, esterases, proteases or lipases, preferably by lipases; even more preferred by a lipase from *Candida Antarctica* [e.g. CALB L (Novozyme)], by a lipase from *Alcaligenes* sp. [e.g. QLM (Meito Sangyo)], by a lipase from *Burkholderia cepacia* (lipase PS) and its mutant lipase AH. The subsequent asymmetric reduction is carried out by oxidoreductases, preferably by ketoreductases or alcohol dehydrogenases, more preferred by the ketoreductases KRED 101, 107, 111, 112, 113 and 114, A1F, B1D and B1E [BioCatalytics]. The required reducing equivalents might be recycled in situ by all state of the art methods; preferably by enzymes; more preferred by glucose dehydrogenase GDH 102 [BioCatalytics]

Suitable buffers are the conventional buffers commonly used in biochemistry in the range of pH 5 to 8, preferably of pH 6 to 7. In the course of the reaction the pH of the reaction mixture is kept constant at the selected value by the addition of a base, preferentially NaOH or KOH-solution. One equivalent is required to neutralize the formed acetic acid and a further equivalent is needed to neutralize the formed gluconic acid.

In the case of the enzyme combination KRED 101, lipase AH and GDH 102 the use of 2-(4-morpholino)-ethane-sulfonic acid buffer (e.g. pH 6.25) in the presence of a non-polar organic solvent such as n-heptane or tert-butyl methyl ether (TBME) (e.g. 20% v/v) and D-glucose (e.g. 0.5M) positively influences overall reactivity.

The reaction temperature may be in a range of 25 to 45° C., preferably 30 to 40° C. The substrate concentration may range from 1-20% (w/w), preferably 5% (w/w).

The low stability of the in situ formed hydroxy ketone (6) requires a catalytic reducing activity in excess of the deacetylation activity. The in situ concentration of the hydroxy ketone (6) has to be high enough enabling high turnover rates for its asymmetric reduction. The ketoreductases display a significantly lower activity towards the direct reduction of the acetoxy ketone (5) in combination with a significantly lower enantiomerically purity for the generated acetoxy alcohol—a potential intermediate towards the diol (7). The process conditions have to suppress the direct reduction of the acetoxy ketone (5) or to enhance the high turnover rates of the asymmetric reduction of the in situ formed hydroxy ketone (6) by triggering its in situ concentration in order to maintain the enantiomerically pure (S)-diol (7).

In another embodiment, the invention refers to a process for the preparation of 2-amido-[5-(1-hydroxy-2-halo-ethyl)]-pyrazines of the formula

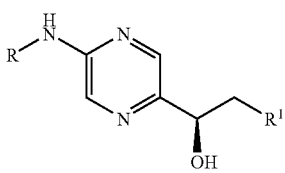

Ib wherein R is lower alkylcarbonyl or an amino protecting group and $R^1$ is halogen, by enzymatic asymmetric reduction of a ketone of the formula

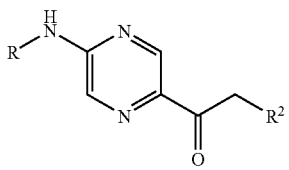

IIb wherein $R^2$ is halogen.

Preferably, $R^1$ and $R^2$ are chlorine.

Preferably, the enzymatic asymmetric reduction is performed by means of one or more oxidoreductases, More preferably, a ketoreductase or an alcohol dehydrogenase is used as oxidoreductase.

In a preferred embodiment, the invention relates to the enzymatic reduction of N-[5-(2-chloro-acetyl)-pyrazinyl]-2,2-dimethyl-propionamide (4) to (S)—N-[5-(2-chloro-1-hydroxy-ethyl)-pyrazin-2-yl]-2,2-dimethyl-propionamide (5).

Scheme 3

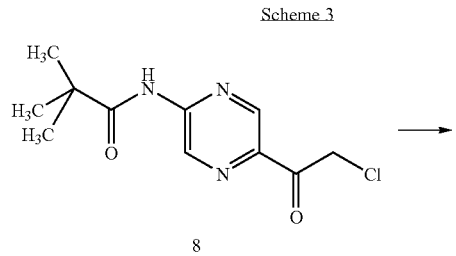

8

-continued

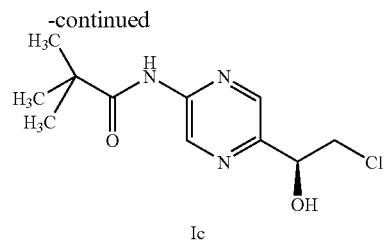

Ic

The asymmetric reduction is carried out by contacting an oxidoreductase with the chloro ketone (8). The required reducing equivalents are applied in catalytic amounts and are recycled in situ.

Preferred oxidoreductases are ketoreductases or alcohol dehydrogenases, more preferred are the ketoreductases KRED 101, KRED 111, KRED 112, KRED 113 and KRED 114 [BioCatalytics]. The required reducing equivalents may be recycled in situ by conventional methods; preferably by enzymes; more preferred by glucose dehydrogenase GDH 102 [BioCatalytics].

Suitable buffers are the conventional buffers commonly used in biochemistry in the range of pH 5 to 8, preferably in the range of 6 to 7. In the course of the reaction the pH of the reaction mixture is kept constant at the selected value by the addition of a base, preferentially NaOH or KOH-solution. One equivalent is required to neutralize the formed gluconic acid.

In the case of the enzyme combination KRED 101 and GDH 102 the use of potassium phosphate buffer (e.g. pH 6.5) in the presence of D-glucose (e.g. 0.06M) at higher substrate concentration and addition of higher D-glucose concentration influences overall reactivity positively.

The reaction temperature may be in a range of 25 to 45° C., preferably in a range of 30 to 35° C. The substrate concentration may range from 0.1 to 10% (w/w), preferably 5% (w/w), more preferably 0.5% (w/w).

Advantageously, the asymmetric reduction of chloro ketone (8) towards the enantiomerically pure (S)—N-[5-(2-chloro-1-hydroxy-ethyl)-pyrazin-2-yl]-2,2-dimethyl-propionamide (Ic) did not need a third hydrolyzing enzyme (e.g. lipase) and did not produce in situ a potential unstable intermediate. The absolute configuration was determined by crystal structure. Subsequently, the enantiomerically chlorinated alcohol (Ic) has to be converted into the desired enantiomerically pure (S)-diol (7) by nucleophilic substitution of chloro against a hydroxyl group.

As already described above, R is preferably tert-butylcarbonyl, i.e. the processes as defined herein before are preferably carried out starting from compounds of formula II, wherein R is tert-butylcarbonyl.

Thus, in another embodiment, the present invention relates to new compounds of the formula

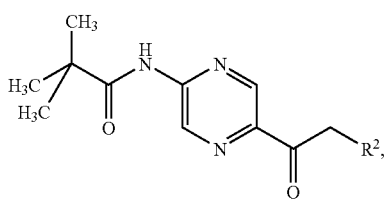

IIc wherein $R^2$ is lower alkylcarbonyloxy or halogen.

The preparation of compounds of formula IIc can be performed according to schemes 4 and 5 below.

In Step 1, the amino group of 2-amino-5-bromopyrazine (1) was protected with trimethylacetyl chloride (pivaloyl chloride; PivCl) in dichloromethane to give amide 7 in 90% yield. Palladium catalyzed carbomethoxylation of amide 2 (step 2) was carried out in a mixed solvent of dimethylformamide:methanol 4:1 under 500 psi of carbon monoxide in a Parr reactor to give methyl ester 9 in 84% yield. In Step 3, Claisen condensation of methyl ester 9 with the enolate generated from tert-butyl acetate by treatment with lithium bis(trimethylsilyl)amide (LHMDS) gave keto ester 10. After extractive workup and solvent exchange, the resulting ethanol solution of 10 was treated with N-bromosuccinimide (NBS) in the presence of a catalytic amount of lithium bromide to give bromide 11 in 95% overall yield from 9. Treatment of 11 with trifluoroacetic acid (TFA) in dichloromethane afforded □-bromo ketone IId in 97% yield (Step 5), the decarboxylation was complete after stirring at room temperature for 40 h. The □-bromo ketone IId was converted to acetoxy ketone IIe by substitution reaction with sodium acetate in DMF at room temperature (step 6). After crystallization from ethyl acetate/heptane, the acetoxy ketone IIe was obtained in 90% yield. Subsequently, it was found that IIe can be precipitated directly from the reaction mixture by the addition of water.

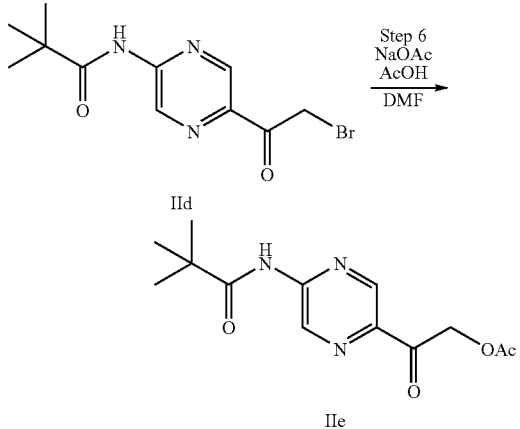

N-[5-(2-Chloro-acetyl)-pyrazin-2-yl]-2,2-dimethyl-propionamide (IIf) can be directly obtained from the methyl ester 9 by reaction with bromochloromethane and activation with butyllithium (see scheme 5).

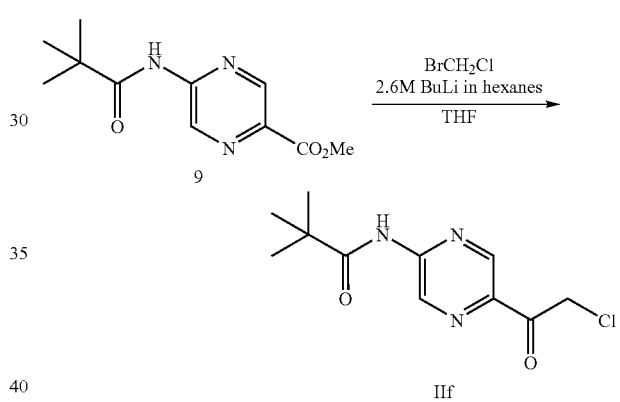

In another embodiment, the invention relates to a new compound of the formula

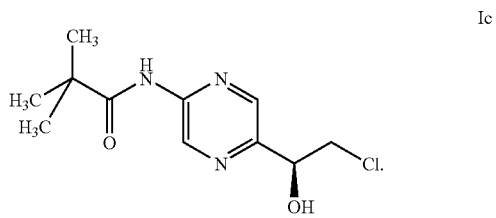

In a further embodiment, the invention provides a process for the preparation of a compound of the formula

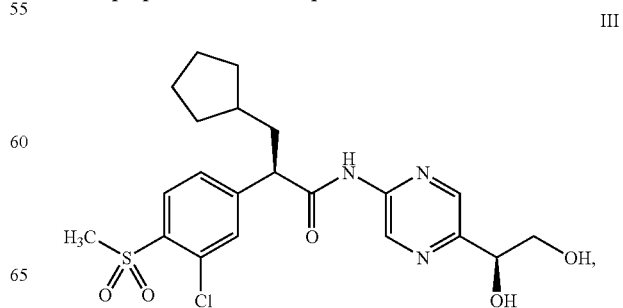

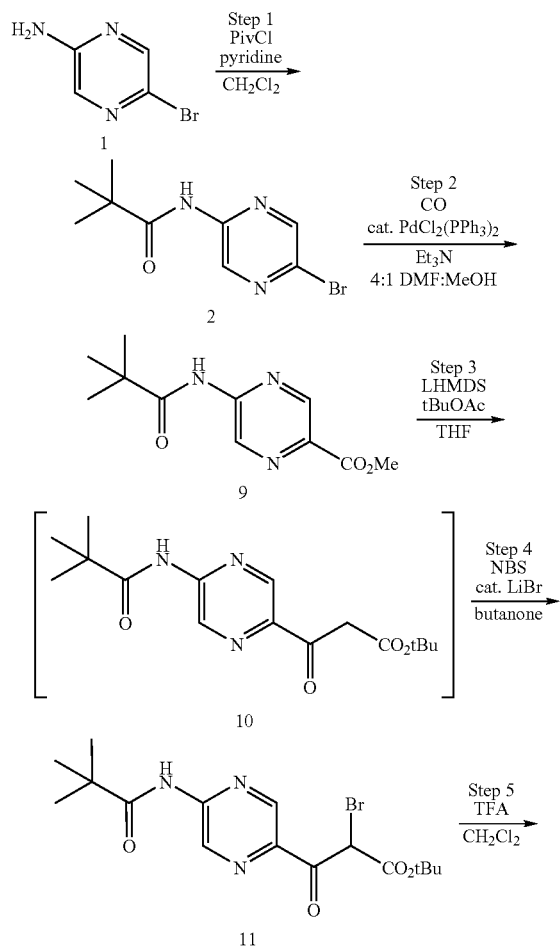

comprising the process according to claims 1 to 11, followed by
a) reaction of the diol of formula Ia

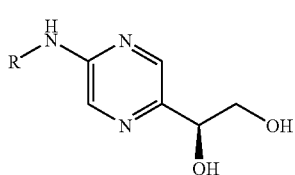

wherein R is lower alkylcarbonyl or an amino protecting group, with 2,2-dimethoxypropane to form an acetal and deprotection of the amine under basic conditions to obtain a compound of formula

IV

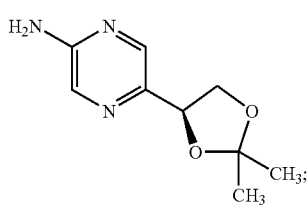

b) condensation of the amine of formula IV with the carboxylic acid of formula

V

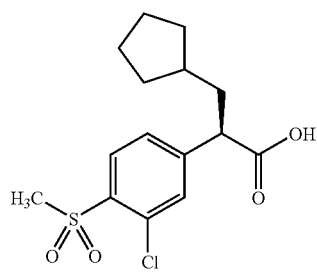

or an activated derivative thereof to obtain the amide; and
c) hydrolysis of the acetal under acidic conditions.

2R-(3-Chloro-4-ethanesulfonyl-phenyl)-3-cyclopentyl-N-[5-(1S,2-dihydroxy-ethyl)-pyrazin-2-yl]-propionamide (the compound of formula II) was found to be a potent glucokinase activator. Compounds that activate GK, and thereby increase the sensitivity of the GK sensor system, are useful in the treatment of the hyperglycemia characteristic of all type II diabetes. Glucokinase activators will increase the flux of glucose metabolism in β-cells and hepatocytes, which will be coupled to increased insulin secretion. Such agents are thus useful for treating type ii diabetes and other metabolic disorders.

In step a), the 1,2-diol group is protected in form of a cyclic acetal, Reaction of the 1,2-diol with dimethoxypropane provides a 1,3-dioxolane. Preferably, the reaction is carried out in the presence of an acid catalyst such as p-toluenesulfonic acid (PTSA) or camphorsulfonic acid (CSA). The acetals are stable to most reaction conditions except protic acids such as aqueous acetic acid, aqueous trifluoroacetic acid and hydrochloric acid and Lewis acids. Thus the acetal will not be attacked by a base such as potassium carbonate which is used for the subsequent deprotection of the amine.

For the condensation in step b), an activated derivative of the carboxylic acid of formula V may be employed, for example a protected ester or acid chloride thereof which may be prepared by methods known to those skilled in the art. Preferably, an acid chloride of the acid of formula V may be used and the coupling will be carried out in the presence of a base such as pyridine or aminopyrazine. The acid chloride can be prepared by reaction of the compound of formula V with oxalyl chloride or thionyl chloride in a suitable solvent such as dichloromethane.

In step c), the acetal protecting group is cleaved under acidic conditions, for example by using hydrochloric acid to obtain the 1,2-diol of formula III In scheme 6 below, the process for the preparation of the compound of formula III starting from a compound of formula Ia as prepared by the enzymatic processes as defined herein before is illustrated.

Scheme 6

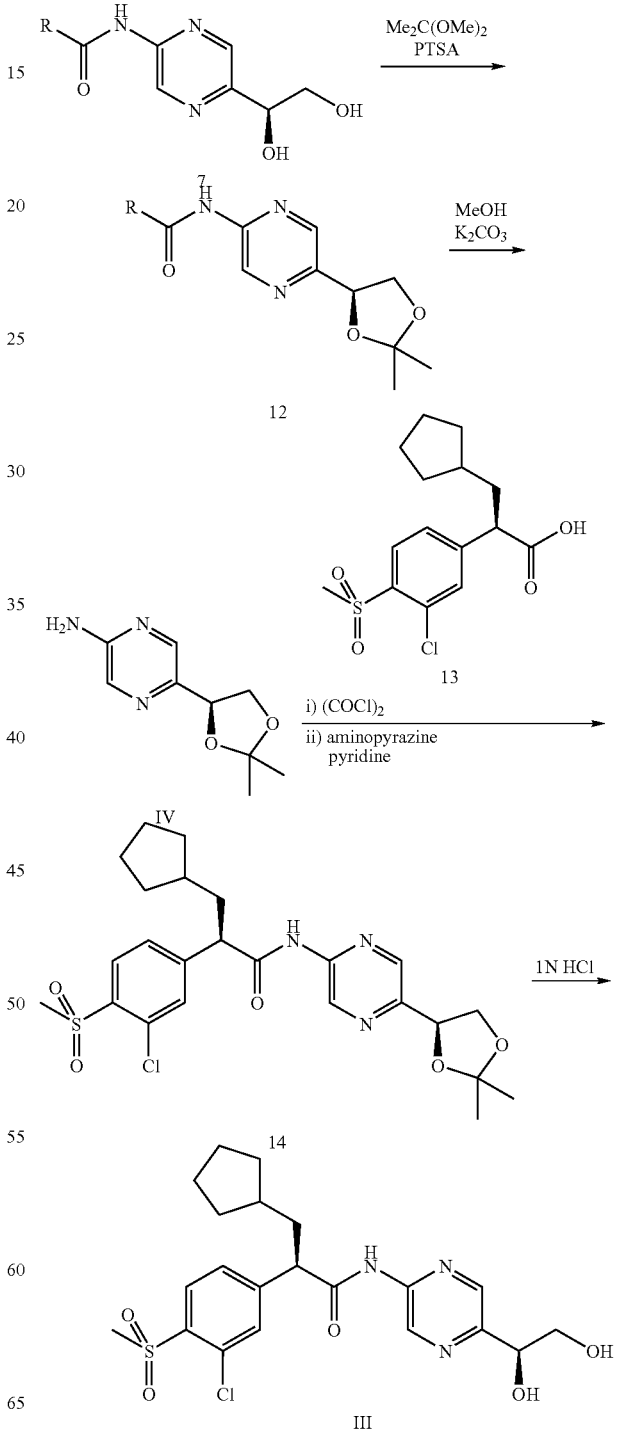

The following examples shall illustrate the invention without limiting it.

EXAMPLES

Example 1

Preparation of acetic acid 2-[5-(2,2-dimethylpropionylamino)-pyrazin-2-yl]-2-oxo-ethyl ester

Step 1: Preparation of N-(5-bromo-pyrazin-2-yl)-2,2-dimethylpropionamide (2)

A 3-necked 1 L round bottomed flask equipped with a magnetic stirrer, thermometer, condenser and nitrogen inlet/outlet was charged with 50.00 g (287.4 mmol) of 2-amino-5-bromopyrazine (1), 218 mL of dichloromethane and 30.50 mL (377.1 mmol) of pyridine. Then, 39.30 mL (319.1 mmol) of trimethylacetyl chloride (PivCl) was added dropwise over 5 min. An exotherm ensued that raised the temperature of the mixture from 22° C. to 44° C. After stirring at ca. 40° C. for 2 h, HPLC analysis indicated complete reaction. The reaction mixture was diluted with 200 mL of ethanol, then concentrated by distillation at atmospheric pressure. After 240 mL of distillate had collected and the temperature of the mixture reached 68° C., 100 mL of water was added slowly, while maintaining the temperature of the mixture at ca. 68° C. After the addition was complete, the resulting suspension was allowed to cool to room temperature and stirred overnight. The solid was collected by filtration, washed with 100 mL of ethanol:water 1:1 and dried by suction to give 67.08 g (90.4% yield) of the title compound as a light beige solid; 98.21% pure as determined by HPLC analysis (HPLC column Zorbax Eclipse XDB-C8, 4.6×50 mm, 1.8 μm, eluent 5-100% acetonitrile/water+01.% TFA over 5 min at 1 mL/min, detection at UV 250 nm, retention time 4.22 min).

Step 2: Preparation of 5-(2,2-dimethyl-propionylamino)-pyrazine-2-carboxylic acid methyl ester (9)

A 300 mL Parr reactor was charged with 15.00 g (58.11 mmol) of the compound prepared in step 1, 16.80 mL (414.8 mmol) of methanol, 67.20 mL of dimethylformamide (DMF), 61.20 mg (0.0872 mmol) of bis(triphenylphosphine) palladium dichloride and 8.900 mL (63.92 mmol) of triethylamine. The reactor was purged twice with nitrogen (by pressurizing it, followed by venting it to atmospheric pressure), then twice with carbon monoxide. The mixture was heated to 92° C., with stirring at 500 rpm, then pressurized with GO to 500 psi for 18 h. HPLC analysis indicated complete reaction. After cooling to 65° C., the reactor was depressurized and the contents were transferred to a 500 mL round bottom flask. The reactor was rinsed with 30 mL of DMF and the rinse was also transferred to the flask. Then, 80 mL of water was added. After cooling to room temperature, the resulting solid was collected by filtration, washed with 50 mL of DMF:water 1:1 and 50 mL of water and dried by suction to give 11.56 g (83.8% yield) of the title compound as a light beige solid; 100% pure as determined by HPLC analysis (same conditions as in step 1, retention time 3.46 min).

Step 3: Preparation of 3-[5-(2,2-dimethylpropionylamino)-pyrazin-2-yl]-3-oxo-propionic acid-tert-butyl ester (10)

A 3-necked 1-L round bottomed flask equipped with a magnetic stirrer, addition funnel, thermocouple probe and nitrogen inlet/outlet was charged with 25.00 mL (185.5 mmol) of tert-butyl acetate, 20.00 g (84.30 mmol) of the compound prepared in step 2 and 20 mL of THF. After cooling to −20° C., a solution of 261.4 mL (261.4 mmol) of 10M lithium bis(trimethylsilyl)amide (LHMDS) in THF was added dropwise, while maintaining the temperature of the reaction mixture between −20° C. and 0° C. The resulting red solution was stirred at −20° C. for 40 min. HPLC analysis indicated complete reaction. The mixture was allowed to warm to 0° C., then quenched by the addition of pre-cooled 200 mL (260.3 mmol) of 25 wt % citric acid solution. The organic layer was separated, washed with 2×200 mL of saturated sodium chloride solution and concentrated at 30° C./60 mmHg to a volume of ca. 50 mL. The concentrated solution was diluted with 200 mL of butanone and again concentrated at 30° C./60 mmHg to ca. 50 mL. The concentrate was again diluted with 200 mL of butanone and concentrated at 30° C./60 mmHg to a volume of ca. 100 mL. NMR analysis indicated the absence of THF. The resulting butanone solution of the title compound was used directly in the next step.

Step 4: Preparation of 2-bromo-3-[5-(2,2-dimethyl-propionylamino)-pyrazin-2-yl]-3-oxo-propionic acid tert-butyl ester (11)

A 1-L round bottomed flask equipped with a magnetic stirrer was charged with 73.00 mg (0.841 mmol) of lithium bromide and the butanone solution obtained in step 3 (ca. 100 mL), which theoretically contained 27.09 g (84.30 mmol) of 3-[5-(2,2-dimethyl-propionylamino)-pyrazin-2-yl]-3-oxo-propionic acid-tert-butyl ester and ca. 73 mL of butanone. To the resulting mixture was added a total of 15.16 g (85.17 mmol) of N-bromosuccinimide portionwise with careful reaction monitoring by HPLC. After stirring at room temperature for 1 h, HPLC analysis indicated complete reaction. The reaction mixture was concentrated at 25° C./25 mmHg to a volume of ca. 70 mL, then diluted with 130 mL of ethyl acetate and washed with 3×100 mL L of water. After concentration at 35° C./60 mmHg to a volume of ca. 90 mL, the resulting suspension was diluted with 200 mL of heptane, and re-concentrated to a volume of ca. 90 mL. Then, 200 mL of heptane was added, and the suspension was again concentrated to a volume of ca. 150 mL. The solid was then collected by filtration, washed with 2×50 mL of heptane and dried by suction to give 32.16 g of the title compound as a light yellow solid; 98.7% pure as determined by HPLC analysis (HPLC column Zorbax XDB-C8, 3×100 mm, 3.5 μm, eluent 20-100% acetonitrile/water+01.% TFA over 10 min at 0.5 mL/min, detection at UV 254 nm, retention time 9.52 min).

Step 5: Preparation of N-[5-(2-bromo-acetyl)-pyrazin-2-yl]-2,2-dimethyl-propionamide (IId)

A 500 mL round bottomed flask equipped with a magnetic stirrer and nitrogen inlet/outlet was charged with 32.10 g (80.19 mmol) of the compound prepared in step 4, 90 mL of dichloromethane and 56.20 mL (756.6 mmol) of trifluoroacetic acid and the reaction mixture was stirred at room temperature for 40 h. HPLC analysis indicated complete reaction. The reaction mixture was concentrated at 30° C./30 mmHg to a volume of ca. 40 mL, diluted with 200 mL of toluene, and concentrated to a volume of ca. 50 mL. The resulting slurry was diluted with 100 mL of toluene and again concentrated to a volume of ca. 50 mL. After diluting with 100 mL of heptane, the solid was collected by filtration and dried by suction to give 23.30 g (96.8% yield) of the title compound as a yellow solid; 99.15% pure as determined by HPLC analysis (same conditions as in step 4, retention time 7.76 min).

Step 6: Preparation of acetic acid 2-[5-(2,2-dimethyl-propionylamino)-pyrazin-2-yl]-2-oxo-ethyl ester (IIe)

A 500 mL round bottomed flask equipped with a magnetic stirrer, addition funnel, thermocouple probe and nitrogen inlet/outlet was charged with 4.40 mL (76.86 mmol) of acetic acid, 140 mL of DMF and 7.000 g (85.33 mmol) of sodium acetate. Then, 23.30 g (77.62 mmol) of the compound obtained in step 5 was added portionwise over 45 min. After stirring at room temperature for an additional 1 h, HPLC analysis indicated complete reaction. The reaction mixture was diluted with 350 mL of ethyl acetate and 100 mL of saturated sodium bicarbonate was added with stirring. The organic layer was separated, washed with 3×100 mL of water and concentrated at 30° C./60 mmHg to a volume of ca. 60 mL. The resulting slurry was diluted with 200 mL of heptane, concentrated at 30° C./60 mmHg to a volume of ca. 150 mL, and stirred at 50° C. for 30 min. After cooling to room temperature, the solid was collected by filtration, washed with 40 mL of 10% ethyl acetate in heptane and dried by suction, then under reduced pressure (house vacuum) for 24 h, to give 19.52 g (90.0% yield) of the title compound as an off-white solid; 98.81% pure as determined by HPLC analysis (same conditions as in step 4, retention time 6.78 min).

$^1$H-NMR (DMSO-$d_6$): 10.71 (s, 1H), 9.37 (d, 1H), 8.89 (d, 1H), 5.48 (s, 2H), 2.14 (s, 3H), 1.25 ppm (s, 9H).

Example 2

Preparation of N-[5-(2-chloro-acetyl)-pyrazin-2-yl]-2,2-dimethyl-propionamide (IIf)

A 3-necked 1-L round bottomed flask equipped with a mechanical stirrer, addition funnel, thermocouple probe and nitrogen inlet/outlet was charged with 24.10 g (102 mmol) 5-(2,2-dimethyl-propionylamino)-pyrazine-2-carboxylic acid methyl ester (9) as prepared in example 1, step 2, 300 mL of THF, and 24.0 mL (369 mmol) of bromochloromethane was added. After cooling to −78° C. using a −90° C. heptane-liquid nitrogen cooling bath, a solution of 100.0 mL (260 mmol) of 2.6 M butyllithium in hexanes was added dropwise, while maintaining the temperature of the reaction mixture at −77±2° C. Then another 15.0 mL (231 mmol) of bromochloromethane was added, followed by the dropwise addition of another 55.0 mL (143 mmol) of 2.6M butyllithium in hexanes, maintaining the temperature of the reaction mixture at −77±2° C. HPLC analysis indicated complete reaction. The cold mixture was poured slowly into 300 mL (300 mmol) of 1N hydrochloric acid and stirred to warm up to ambient temperature. The mixture was the partially concentrated under vacuum and the precipitated solids were isolated by filtration, washed with water and dried by suction to give 19.42 g of crude product as a light orange solid, 91.5% pure as determined by HPLC analysis. This crude product, 19.0 g, was slurried in 100 mL of ethyl acetate and the resulting suspension was diluted with 50 mL of heptane. The solid was then collected by filtration, washed with 2×50 mL of heptane-ethyl acetate 1:1 and dried by suction to give 13.5 g (53% yield) of the chloroketone as an off-white solid, >99% pure as determined by HPLC analysis.

$^1$H-NMR (DMSO-$d_6$): 10.71 (s, 1H), 9.35 (d, 1H), 8.94 (d, 1H), 5.20 (s, 2H), 1.25 ppm (s, 9H).

Example 3

Fermentation and Biotransformation

2×500 ml baffled flasks containing 100 ml of 508S medium comprising per L de-ionized water: glucose 20 g, yeast extract 10 g and soytone 10 g was inoculated with 1 mL of a frozen stock of C. parapsilosis R 2599. The flask is then incubated at 27° C. for 72 hours on an orbital shaker set to 220 rpm. The contents of the flask are then pooled into a suitable inoculation flask and inoculated into a 7.5 L fermenter containing 5 L of YSD medium comprising per L de-ionized water: glucose 20 g, yeast extract 10 g, soytone 10 g and yeast nitrogen base without amino acids 6.7 g and Shell Aseol antifoam 0.3 ml. The fermentation parameters were set as follows: Temperature 27° C., dissolved oxygen was maintained above 50% by automatic adjustment of aeration and stirring speed, pH was maintained at 6.5 by automatic addition of 25% w/v ammonium hydroxide, ethanol (100%) was fed using a dosimeter at a rate of 4-5% v/v per day. After 20 h cultivation 1.5 L of broth was removed and ethanol feeding started. After a further 2 hours 175.5 g of acetic acid 2-[5-(2,2-dimethylpropionylamino)-pyrazin-2-yl]-2-oxo-ethyl ester (Example 1) was added as a suspension in 875 mL of water to give a final concentration of 5% (w/v). Periodically samples were removed and analyzed by HPLC to determine the titre of (S)—N-[5-(1,2-dihydroxy-ethyl)-pyrazin-yl]-2,2-dimethyl-propionamide (7) and also the enantiomeric purity of this product. When the reaction was judged complete after 68 hours the C. parapsilosis was inactivated by heating the broth in situ to 70° C. for 30 minutes.

TABLE 1

| Reaction Time (h) | Diol (g/L) | R-Diol (%) | S-Diol (%) |
|---|---|---|---|
| 1 | 1.0 | | |
| 3 | 3.4 | | |
| 20 | 17.0 | | |
| 24 | 17.0 | | |
| 26 | 17.6 | | |
| 44.5 | 27.2 | | |
| 51 | 32.3 | | |
| 68 | 30.7 | 3.6 | 96.4 |

Isolation

The heat inactivated broth as obtained above was used for product isolation. 4.23 L broth was centrifuged on a laboratory centrifuge with swing-out rotors (3500 rpm, 15 min). The opalescent supernatant (3.60 L) was removed. The pellet was re-suspended in 0.8 L water and centrifuged, giving 0.76 L turbid supernatant. The unified aqueous solutions were extracted three times with ethyl acetate (each 9 L). At the first extraction a spontaneous phase separation occurred. At the second extraction an emulsion was obtained. The emulsion was broken by mixing in 250 g dicalite speed plus (Acros Organics 123380010) and filtering the mixture in vacuo (Filtrox filter plate AF 50/8427). At the third extraction a fast phase separation was obtained. The obtained organic extracts were pooled and concentrated in vacuo on a laboratory rotavap. The concentrate was mixed with two spoons of dicalite speed plus, filtered and made up to 1.00 L concentrate with ethyl acetate. The concentrate contained 114.4 g (s)-diol (7).

A sample of the concentrate was dried and showed following analytical data: (HPLC): 99.4% by area purity by HPLC (column SupelcoSil ABZ+, 4.6×250 mm, 5 µm, eluent 20-90% acetonitrile/water+0.1% TFA over 10 min at 1 mL/min, detection at UV 300 nm, retention time 4.26 min), 92.0% ee by chiral HPLC (column Chiralpak AD-H, eluent 20% ethanol/80% acetonitrile at 1 mL/min, 40° C., detection at UV 237 nm, retention time: 18.14 min (R-diol) and 20.86 min (S-diol)).

$^1$H-NMR (DMSO-$d_6$): 10.15 (s, 1H), 9.18 (s, 1H), 8.44 (s, 1H), 5.54 (d, 1H), 4.72 (t, 1H), 4.63 (dd, 1H), 3.69 (m, 1H), 3.53 (m, 1H), 1.25 ppm (s, 9H).

MS (Ion Spray): m/z 240.1 (M+H for M 239.1).

Example 4

Large Scale Multi-Enzymatic Reaction 50 g of acetic acid 2-[5-(2,2-dimethylpropionylamino)-pyrazin-2-yl]-2-oxo-ethyl ester (178 mmol) was stirred in 150 ml tert-butyl methyl ether (TBME). Subsequently the reaction buffer, 674 mL 20 mM of 2-(4-morpholino)-ethansulfonic acid, and 100.1 g of D-glucose (658 mmol) were added. The temperature was adjusted to 29° C. and the pH to 6.25. The reaction—deacetylation—was started by the addition of 2.01 g lipase AH. Directly afterwards, 40 mg of glucose dehydrogenase GDH 102, 201 mg of ketoreductase KRED 101 and 202 mg of cofactor NADP were added to initiate the asymmetric reduction. The reaction temperature was increased up to 37° C. The stirred suspension was maintained at pH 6.25 (and 37° C.) by the controlled addition (pH-stat) of 1.0 N sodium hydroxide solution. After 11.2 h, after a total consumption of 354.1 mL of 1.0 N sodium hydroxide, and after complete conversion, the reaction mixture was stirred for further 10.5 h. For the product extraction 300 g of sodium chloride were added into the reaction mixture and the pH was adjusted to 7.5. Subsequently, the reaction mixture was extracted 5 times with 1 L of ethyl acetate. The phase separation occurred spontaneously. The combined organic phases were dried over anhydrous sodium sulfate, evaporated and dried on HV over night. 44.76 g (S)—N-[5-(1,2-dihydroxy-ethyl)-pyrazin-yl]-2,2-dimethyl-propionamide (4) (96.4% HPLC purity, [SupelcoSil ABZ+, 250×4.6 mm, eluent 20-90% acetonitrile/water+0.1% TFA over 10 min at 1 mL/min, detection at UV 300 nm, retention time 5.3 min], ee>99.9% [Chiralpak IA, 250×4.6 mm, 5 µm, eluent 50% Heptane 50% Ethanol/Methanol 1:1 over 20 min at 1 mL/min, detection at UV 240 nm, retention time enantiomers 9.3 and 10.9 min]) were isolated as a light orange, highly viscous oil.

Example 5

Small Scale Reductions of Acetic Acid 2-[5-(2,2-dimethylpropionylamino)-pyrazin-2-yl]-2-oxo-ethyl ester 2 mg of acetic acid 2-[5-(2,2-dimethylpropionylamino)-pyrazin-2-yl]-2-oxo-ethyl ester were dissolved in 20 µl DMSO and added into reaction vials containing 20 µl of 2-propanol, 1.5 ml of 100 mM 2-(4-morpholino)-ethane-sulfonic acid, pH 6.0, 3 mg of NADPH and 3 mg of a ketoreductase (see table 1). After 2h the reactions were extracted with 0.5 ml ethyl acetate and analyzed via chiral HPLC ([Chiralcel OD-H, 250×4.6 mm, Nr.146, eluent 65% heptane 20% heptane+0.1% TFA 15% iso-propanol, 40° C. over 15 min at 1 mL/min, detection at UV 210 nm, retention time enantiomers 6.2 and 7.2 min], results see table 2).

TABLE 2

Selected analytical results of the formation of the corresponding acetoxy alcohol (acetic acid 2-[5-(2,2-dimethylpropionylamino)-pyrazin-2-yl]-2-hydroxy-ethyl ester)

| KRED ketoreductase | Conversion Area % | ee acetoxy alcohol % |
|---|---|---|
| 101 | 33 | 73.7 |
| 107 | 0 | n.d. |
| 111 | 39.6 | 68.4 |
| 112 | 46.7 | 70.8 |
| 113 | 28.5 | 70.4 |
| 114 | 42.7 | 65.4 |
| A1F | 1.0 | n.d. |
| B1D | 13.6 | 79.5 |
| B1E | 0 | n.d. |

Example 6

Small Scale Multi Enzymatic Reactions 1 mg of acetic acid 2-[5-(2,2-dimethylpropionylamino)-pyrazin-2-yl]-2-oxo-ethyl ester (IIe) were dissolved in 20 µl DMSO and added into reaction vials containing 20 µl of 2-propanol, 1.5 ml of 100 mM potassium phosphate, pH 7.2, 3 mg of NADPH, 30 µl of Lipozyme CALB L [Novozyme] and 2 mg of a ketoreductase (see table 2). After 16 h the reactions were extracted with 0.5 ml ethyl acetate and analyzed via chiral HPLC (Chiralcel AD-H, Nr.417, eluent 90% ethanol 10% methanol, 40° C. over 30 min at 1 mL/min, detection at UV 210 nm, retention time enantiomers 9.2 and 10.2 min), result see table 3).

TABLE 3

Selected analytical results of the formation of the corresponding (S)-diol (4)

| KRED ketoreductase | Conversion Area % | ee diol % |
|---|---|---|
| 101 | 97.6 | 99 |
| 107 | 97.3 | >99 |
| 111 | 97.9 | 99.5 |
| 112 | 97.8 | >99 |
| 113 | 97.9 | >99 |
| 114 | 97.3 | 98 |
| A1F | 97.5 | >99 |
| B1D | 97.4 | >99 |
| B1E | 97.4 | >99 |

Example 7

Enzymatic Reduction of N-[5-(2-chloro-acetyl)-pyrazin-2-yl]-2,2-dimethyl-propionamide (IIf)

1.5 g of N-[5-(2-chloro-acetyl)-pyrazin-2-yl]-2,2-dimethyl-propionamide (example 2, 5.8 mmol) was placed into a reactor equipped with a pH electrode, a pH controlled dosing pump and a stirrer. Subsequently the reaction buffer, 300 ml of 100 mM potassium phosphate buffer and 3.5 g of D-glucose (17.7 mmol) were added. The temperature was adjusted to 30° C. and the pH to 6.5. The asymmetric reduction was started by the addition of 25 mg of glucose dehydrogenase GDH 102,100 mg of ketoreductase KRED 101 and 250 mg of cofactor NADP. The pH was maintained at pH 6.5 (and 30° C.) by the controlled addition (pH-stat) of 1,0 N sodium hydroxide solution. After 46 h, after a total consumption of 5.79 mL of 1.0 N sodium hydroxide, the reaction was clarified by filtration. Subsequently, the product was extracted with 0.4 L of ethyl acetate. The phase separation occurred spontaneously. The organic phase was dried over anhydrous sodium sulfate, evaporated and dried on HV over night. 1.42 g (S)-chloro alcohol (97.7% HPLC purity, [Suplecosil Abz+, 250*4.6 mm, eluent 35-90% acetonitrile/water+0.1% TFA, 25° C. over 10.9 min at 1 mL/min, detection at UV 300 nm, retention time 5.6 min], ee>99.9% [Chiralcel OD-H, 250*4.6 mm, eluent 85% heptane 15% ethanol+0.01 M ammonium acetate, 25° C. over 25 min at 0.8 mL/min, detection at UV 302 nm, retention time enantiomers 6.6 and 7.5 min]) was isolated as light yellow crystals.

$^1$H-NMR (DMSO-d$_6$): 10.21 (s, 1H), 9.2 (d, 1H), 8.50 (d, 1H), 6.10 (d, 2H), 4.94 ppm (d/tr, 1H), 3.92 (d/d, 2H), 1.25 ppm (s, 9H).

MS (Ion Spray). m/z 257.8 (M+H for M 257.1).

Example 8

Preparation of 2(R)-(3-chloro-4-methanesulfonyl-phenyl)-3-cyclopentyl-N-[5-(1 (S), 2-dihydroxy-ethyl)-pyrazin-2-yl]-propionamide (III)

Step 1: Preparation of N-[5-((S)-2,2-dimethyl-[1,3] dioxolan-4-yl)-pyrazin-2-yl]-2,2-dimethyl-propionamide (12)

A solution of N-[5-(1 (S),2-dihydroxy-ethyl)-pyrazin-2-yl]-2,2-dimethyl-propionamide (46 g slightly wet with solvent, ~170 mmol) in tetrahydrofuran (275 mL) was treated with 2,2-dimethoxypropane (225 mL, 1.88 mol) and ρ-toluenesulfonic acid monohydrate (3.4 g, 17.9 mmol). The reaction mixture was stirred at 25° C. for 16.5 h. Thin layer chromatography showed that the reaction was complete to form a less polar product. The reaction mixture was concentrated in vacuo, and the residue was dissolved in methylene chloride (600 mL). The organic layer was washed with a saturated aqueous sodium chloride solution (250 mL) and a saturated aqueous sodium bicarbonate solution (250 mL). Each aqueous layer was back-extracted with methylene chloride (250 mL). The combined organic layers were stirred with sodium sulfate (35 mg) and Norit A Charcoal (8 g) and then filtered through a pad of celite. The filtrate was concentrated in vacuo to a weight of about 250 g. The material was treated with diethyl ether (300 mL), and the mixture again was concentrated in vacuo to a weight of about 350 g, at which time, crystallization began. The mixture was stored in a refrigerator (4° C.) for 4 h and filtered. The solids were dried in a vacuum oven at 30° C. for 16 h to afford white crystals (32.3 g, 68%), mp 144-144.5° C. Collection of an additional crop from the mother liquor afforded white crystals (9.5 g, 20%) which were comparable in purity to the first crop. High-performance liquid chromatography analysis with a chiral column indicated both crops were 100% ee as compared to an authentic racemate sample. The two crops were combined to afford the desired N-[5-((S)-2,2-dimethyl-[1,3]dioxolan-4-yl)-pyrazin-2-yl]-2,2-dimethyl-propionamide.

Step 2: Preparation of 5-((S)-2,2-dimethyl-[1,3]dioxolan-4-yl)-pyrazin-2-ylamine (13)

A mixture of N-[5-((S)-2,2-dimethyl-[1,3]dioxolan-4-yl)-pyrazin-2-yl]-2,2-dimethyl-propionamide (8.4 g, 30.7 mmol) and potassium carbonate (4.32 g, 31.2 mmol) in methanol (150 mL) was stirred at 25° C. for 16.5 h, at which time, thin layer chromatography suggested partial conversion to a more polar product. In an effort to avoid epimerization at the stereogenic center, the reaction was discontinued before completion. Therefore, the solvent was removed under reduced pressure at 25° C. The resulting residue was again concentrated in vacuo from ethyl acetate (50 mL). The material was purified using Biotage chromatography (FLASH 40 L, Silica, ethyl acetate). The early fractions collected allowed for the recovery of unreacted starting pivaloylamide as a white solid (2.0 g, 24%). The later fractions were concentrated in vacuo to provide 5-((S)-2,2-dimethyl-[1,3]dioxolan-4-yl)-pyrazin-2-ylamine (3.7 g, 63%) as a pale yellow oil. High-performance liquid chromatography analysis with a chiral column indicated 100% ee.

Step 3: Preparation of 2(R)-(3-chloro-4-methanesulfonyl-phenyl)-3-cyclopentyl-N-[5-((S)-2,2-dimethyl-[1,3]dioxolan-4-yl)-pyrazin-2-yl]-propionamide (14)

A solution of 2(R)-(3-chloro-4-methanesulfonyl-phenyl)-3-cyclopentyl-propionic acid (prepared as in Example 1, 6.29 g, 19.01 mmol) and N,N-dimethylformamide (2 drops) in methylene chloride (70 mL) was stirred at 2° C. and then treated with oxalyl chloride (4.15 mL, 45.7 mmol). The mixture was stirred at 2° C. for 5 min and at 25° C. for 15 min. The reaction mixture was then concentrated in vacuo. The residue was dissolved in benzene (25 mL), and the evaporation was repeated. The resulting acid chloride was dissolved in methylene chloride (40 mL), cooled to at 0° C., and then treated with a solution composed of 5-((S)-2,2-dimethyl-[1,3]dioxolan-4-yl)-pyrazin-2-ylamine (3.65 g, 18.95 mmol), pyridine (4.6 mL, 56.9 mmol) and methylene chloride (40 mL). The mixture was stirred for 16 h without replenishing the cooling bath. The reaction mixture was then treated with a 1N aqueous hydrochloric acid solution (100 mL). The layers were separated, and the aqueous layer was extracted with methylene chloride (75 mL). The organic layers were washed with a saturated aqueous sodium bicarbonate solution (100 mL) and a saturated aqueous sodium chloride solution. The combined organic layers were dried over sodium sulfate, filtered, and concentrated in vacuo. Biotage chromatography (FLASH 40 L, Silica, 1/1 ethyl acetate/hexanes) afforded 2(R)-(3-chloro-4-methanesulfonyl-phenyl)-3-cyclopentyl-N-[5-((S)-2,2-dimethyl-[1,3]dioxolan-4-yl)-pyrazin-2-yl]-propionamide (8.9 g, 92%) as a white foam: (ES)$^+$-HRMS m/e calcd for $C_{24}H_{30}CiN_3O_5S$ (M+H)$^+$ 508.1668, found 508.1671.

Step 4: Preparation of 2(R)-(3-chloro-4-methanesulfonyl-phenyl)-3-cyclopentyl-N-[5-(1(S),2-dihydroxy-ethyl)-pyrazin-2-yl]-propionamide (III)

A solution of 2(R)-(3-chloro-4-methanesulfonyl-phenyl)-3-cyclopentyl-N-[5-((S)-2,2-dimethyl-[1,3]dioxolan-4-yl)-pyrazin-2-yl]-propionamide (8.85 g, 17.4 mmol) in tetrahydrofuran (50 mL) was treated with a 1N aqueous hydrochloric acid solution (50 mL). The resulting milky reaction mixture was stirred at 25° C., and within 15 min, the milky reaction mixture became clear. The stirring was continued at 25° C. for 16 h. The reaction was concentrated in vacuo, and the residue was extracted with methylene chloride (1×100 mL then 2×50 mL). Each organic extract was washed with a saturated aqueous sodium bicarbonate solution (50 mL) and a saturated aqueous sodium chloride solution (50 mL). The combined organic layers were dried over sodium sulfate, filtered, and concentrated in vacuo. Biotage chromatography (FLASH 40 L, Silica, 1/1 ethyl acetate/hexanes then 100% ethyl acetate) afforded 2(R)-(3-chloro-4-methanesulfonyl-phenyl)-3-cyclopentyl-N-[5-(1 (S),2-dihydroxy-ethyl)-pyrazin-2-yl]-propionamide (7.15 g, 88%) as a colorless foam. (ES)⁺-HRMS m/e calcd for $C_{21}H_{26}ClN_3O_5S$ (M+H)⁺ 468.1355, found 468.1360.

It is to be understood that the invention is not limited to the particular embodiments of the invention described above, as variations of the particular embodiments may be made and still fall within the scope of the appended claims.

What is claimed is:

1. A method for the preparation of a compound of formula I:

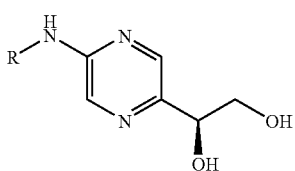

by the enzymatic hydrolysis and enzymatic asymmetric reduction of a ketone of formula II:

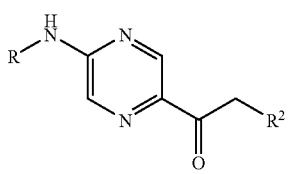

wherein R is a lower alkylcarbonyl or an amino protecting group and $R^2$ is alkylcarbonyloxy, comprising the step of contacting the compound of formula II with a yeast of the species *Candida parapsilosis*.

2. A method for the preparation of a compound of formula III:

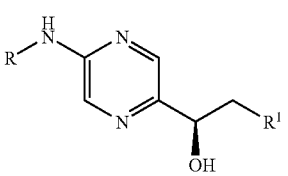

by the enzymatic asymmetric reduction of a ketone of formula IV:

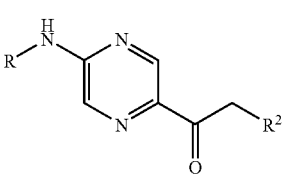

wherein R is a lower alkylcarbonyl or an amino protecting group and $R^1$ and $R^2$ are a halogen, comprising the step of contacting the compound of formula II with one or more oxidoreductases.

3. The method of claim 2, wherein the oxidoreductase is a ketoreductase or an alcohol dehydrogenase.

4. The method for the preparation of a compound of formula I:

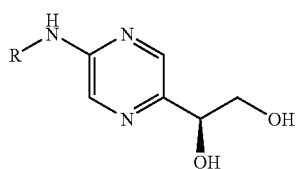

comprising contacting a compound of formula III:

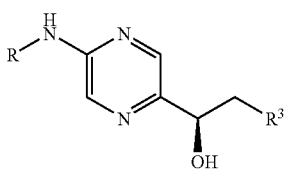

wherein R is a lower alkylcarbonyl or an amino protecting group and $R^1$ is halogen, with a source of a hydroxyl group.

5. A method for the preparation of a compound of formula I:

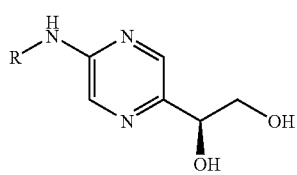

by the enzymatic hydrolysis and enzymatic asymmetric reduction of a ketone of formula II:

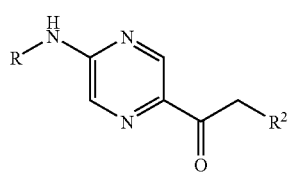

wherein R is a lower alkylcarbonyl or an amino protecting group and $R^2$ is alkylcarbonyloxy, comprising contacting the compound of formula II with a hydrolase selected from the group consisting of an esterase, a protease and a lipase; and one or more oxidoreductases.

6. The method of claim 5, wherein the hydrolase is a lipase.

7. The method of claim 6, wherein the lipase is obtained from *Candida antarctica*, *Alcaligenes* sp. or *Burkholderia cepacia*.

8. The method of claim 5, wherein the oxidoreductase is an alcohol dehydrogenase or a ketoreductase.

9. The method of claim 8, wherein the ketoreductase is selected from the group consisting of KRED101, KRED107, KRED111, KRED112, KRED113, KRED114, A1F, B1D and B1E in combination with glucose dehydrogenase 102 (GDH102).

10. A method for the preparation of a compound of formula V:

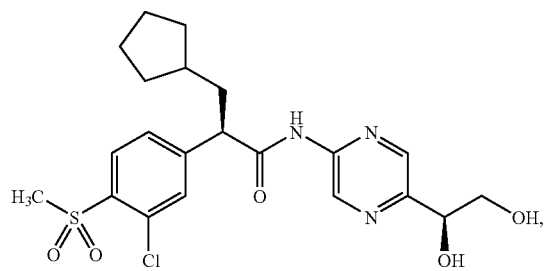

V comprising making the compound of formula I, wherein R is a lower alkylcarbonyl or an amino protecting group:

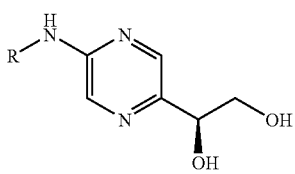

I by the method of claim 1, 4 or 5, further comprising
(a) reacting the compound of formula I with 2,2-dimethoxypropane to form an acetal and deprotecting the amine under basic conditions to obtain a compound of formula VI:

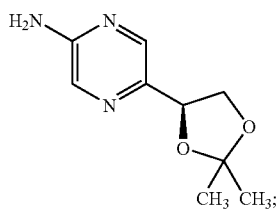

VI (b) condensing the amine of formula VI with a carboxylic acid of formula VII:

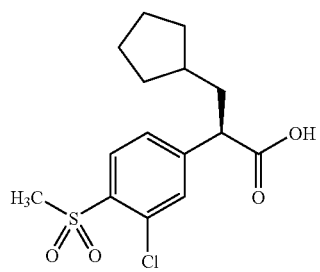

VII to obtain an amide; and
(c) hydrolyzing the acetal of the amide under acidic conditions to obtain the compound of formula V.

11. A compound of formula:

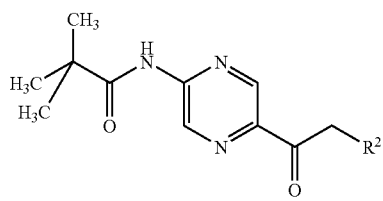

VIII wherein $R^2$ is a lower alkylcarbonyloxy or halogen.

12. The compound according to claim 11, wherein $R^2$ is acetyloxy or halogen.

13. A compound of formula:

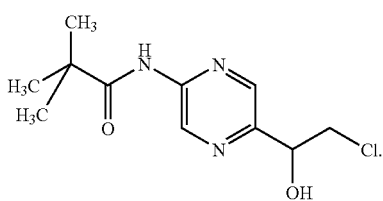

IX

* * * * *